United States Patent [19]

Binder

[11] Patent Number: 4,814,330

[45] Date of Patent: Mar. 21, 1989

[54] 3-PHENYL-1-PROPANONES, PROCESS OF PREPARING THEREOF AND METHOD OF TREATING ARRHYTHMIAS

[76] Inventor: Dieter Binder, Sieveringerstrasse 207, A-1190 Vienna, Austria

[21] Appl. No.: 24,798

[22] Filed: Mar. 11, 1987

[30] Foreign Application Priority Data

Oct. 29, 1986 [AT] Austria ............................ 2870/86

[51] Int. Cl.$^4$ .................... A61K 31/38; C07D 333/32
[52] U.S. Cl. ................................ 514/231.5; 514/212; 514/252; 514/326; 514/422; 514/445; 540/597; 544/146; 544/379; 546/212; 548/527; 549/64
[58] Field of Search .............. 514/326, 230, 252, 445, 514/212, 422; 546/212; 544/146, 379; 549/64; 540/597; 548/527

[56] References Cited

U.S. PATENT DOCUMENTS 4,352,819 10/1982 Binder .................................. 549/64

Primary Examiner—Alan Siegel
Attorney, Agent, or Firm—Spencer & Frank

[57] ABSTRACT

Therapeutically useful 1-[3-(2-dialkylaminoethoxy)-2-thienyl]-3-phenyl-1-propanones of the formula

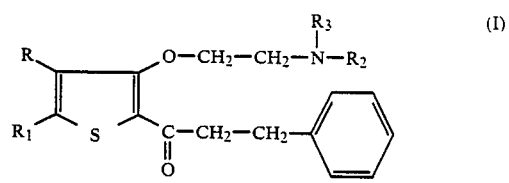

and acid addition salts thereof, wherein R and $R_1$ each are hydrogen or methyl, $R_2$ and $R_3$, which are the same or different, each are alkyl, cycloalkyl, alkenyl or alkynyl each containing up to 8 carbon atoms, or $R_2$ and $R_3$ together with the nitrogen atom to which they are attached form a 5 to 7-membered saturated ring or a saturated heterocyclic ring which may contain optionally an oxygen or nitrogen atom as further hetero atom in the ring, a further nitrogen atom being unsubstituted or substituted by an alkyl radical containing 1 to 3 carbon atoms.

The compounds are useful for the treatment of various disturbances of the heart rhythm.

14 Claims, No Drawings

3-PHENYL-1-PROPANONES, PROCESS OF PREPARING THEREOF AND METHOD OF TREATING ARRHYTHMIAS

BACKGROUND OF THE INVENTION

1. Field of the Invention

This invention relates to compounds derived from 1-[3-(2-dialkylaminoethoxy)-2-thienyl]-3-phenyl-1-propanone, acid addition salts thereof, a process for preparing the compounds thereof, pharmaceutical compositions thereof and a method of treating arrhythmias with the novel compounds.

SUMMARY OF THE INVENTION

The present invention provides new therapeutically valuable 1-[3-(2-dialkylaminoethoxy)-2-thineyl]-3-phenyl-1-propanones of the formula

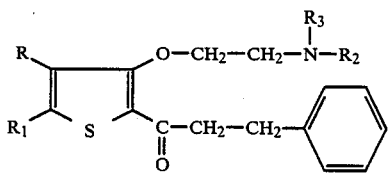

and their acid addition salts, wherein R and $R_1$ each are hydrogen or methyl and $R_2$ and $R_3$, which are same or different, each are alkyl, cycloalkyl, alkenyl or alkynyl each containing up to 8 carbon atoms, or $R_2$ and $R_3$ together with the nitrogen atom to which they are attached from a 5 to 7-membered saturated ring or a saturated heterocyclic ring which may contain optionally an oxygen or nitrogen atom as further hetero atom, an additional nitrogen atom being unsubstituted or substituted by an alkyl group containing 1 to 3 carbon atoms.

This invention also relates to a pharmaceutical composition comprising an antiarrhythmic amound of the novel compounds described hereinabove and a pharmaceutical acceptable carrier.

Due to the above mentioned pharmacological properties, the compounds of the invention or their acid addition salts may be used for treating disorders of the cardiocirculatory system, especially for treating disturbances of the heart rhythm alone, or in a mixture with each other or with other active ingredients in the form of regular pharmaceutical preparations and also in the form of slow release preparations.

The present invention also relates to a process for the preparation of the compounds of formula (I). The process of the invention comprises reacting a compound of the formula

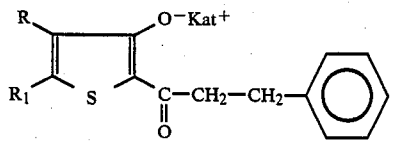

wherein R and $R_1$ are as defined above and $Kat^+$ is an alkali metal or a quaternary ammonium ion, with a compound of the formula

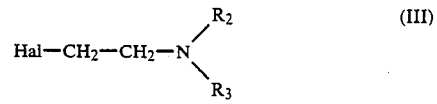

wherein Hal is chlorine, iodine or bromine and $R_2$ and $R_3$ are as defined above, in an inert solvent.

Optionally, the process also comprises converting the thus obtained bases of formula (I) to a pharmaceutically acceptable acid addition salt thereof by adding a pharmaceutically acceptable acid.

This invention also provides a method of treating a cardiac arrhythmia comprising administering to a patient in need of such treatment an antiarrhythmic amount of the pharmaceutical composition of the invention.

Other objects, advantages and features of the present invention will become apparent to those skilled in the art from the following discussion.

DESCRIPTION OF THE PREFERRED EMBODIMENTS

The compounds of the invention possess excellent anti-arrhythmic activity, especially when they are administered by the oral route.

Among the types of tachycardias which may be treated with the present compounds are supraventricular tachycardia, ventricular tachycardia, ventricular ectopia and reentry tachycardia. However, other types of tachycardias are also contemplated for treatment with the inventive compounds.

A suitable dose for administering the novel compounds is between about 2 mg/Kg and 10 mg/Kg per day. However, other doses are also contemplated within the confines of the invention. The novel compounds may be administered in several doses and by the oral route.

The starting compounds of formulae (II) are known from the literature as can be seen, e.g., from the specification of the Austrian Pat. No. 369 739.

Also the compounds of formula (III) are known from the literature (see the references given in the examples) or may be prepared from the known compounds (IV), e.g.

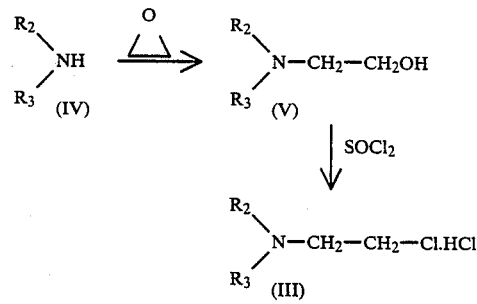

The acid addition salts of the end compounds may be converted into the free bases in a known manner, e.g., by addition of an alkali or by means of ion-exchangers. Additional salts may be formed therefrom by reacting the same compounds with inorganic or organic acids, especially those suitable to form therapeutically useful and pharmaceutically acceptable salts.

Suitable acids to form the acid addition salts of the novel compounds are acids which form pharmaceutically acceptable salts with the compounds of the invention such as inorganic and organic acids.

Examples of such acids are hydrochloric acid, hydrobromic acid, phosphoric acid, sulfuric acid, citric acid, acetic acid, succinic acid, maleic acid, p-toluenesulfonic acid, methanesulfonic acid and the like. However, other acids can also be employed.

The novel compounds may be present in the pharmaceutical compositions in an amount between about 100 mg/tablet and 200 mg/tablet, the remainder being a pharmaceutically acceptable filler as is known in the art.

The composition may be dispensed in other forms besides tablets, such as film tablets, capsules, microcapsules, slow release compositions and others known in the art as suitable for oral administration of medicines.

In the process for obtaining the novel compounds it is preferred to heat the corresponding acids of the compounds of formula (II) and the compounds of formula (III) in an inert solvent in the presence of an excess of anhydrous alkali carbonates to reflux.

Examples of such solvents are toluene, dimethylcarbonate, diethylcarbonate or ketones, such as methyl ethyl ketone.

If higher boiling solvents are used the temperature should not exceed 130° C.

This reaction step is suitable conducted for a period of time between about 12 hours and 40 hours. The step, however, may be allowed to proceed for a different length of time as well dependent on the reaction temperature and the nature of the used solvent.

Since the corresponding acids of the compounds of formula (II) possess relatively strong acid properties the alkali salts of said compounds form already under the mentioned reaction conditions, which salts then react with the compounds of formula (III) in a Williams-Ether-Synthesis. According to a process variant it would be also possible to prepare separately the alkali salts by means of alkali hydrides, alkali hydroxides, alkali alcoholates or quaternary ammonium hydroxides and to react them subsequently with the compounds of formula (III) in the mentioned solvents.

Since in the most cases the free bases of formula (I) are oils difficult to crystallize it is advisable to effect the purification by means of acid addition compounds easy to crystallize such as the hydrochlorides.

Such acid addition salts may be converted into the free bases in a manner known per se, e.g. with alkalis or ion exchangers. By reaction of said bases with inorganic or organic acids, especially those suitable for the formation of therapeutically useful salts, further salts may be obtained.

Due to the close relationship between the new compounds and the salts thereof it is clear that a reference to free bases should include also the corresponding salts.

Having now generally described this invention, the same will be better understood by reference to certain specific examples, which are included herein for purposes of illustration only and are not intended to be limiting of the invention or any embodiment thereof, unless so specified.

EXAMPLE 1

1-[3-(2-Diethylaminoethoxy)-4-methyl-2-thienyl]-3-phenyl-1-propanone hydrochloride (I) ($R_1 = H$, $R_2 = CH_3$, $R_2$ and $R_3 =$ ethyl)

4.9 g of 2-diethylaminoethylchloride hydrochloride are partitioned between 10 ml of toluene and 20 ml of a concentrated solution of potassium carbonate. The organic phase is separated, dried with sodium sulfate and added to a solution of 2 g (8.12 mmoles) of 1-(3-hydroxy-4-methyl-2-thienyl)-1-propanone in 35 ml of absolute toluene. 3.0 g of anhydrous potassium carbonate are added to the obtained mixture and the mixture is heated to reflux with stirring for 22 hours. After cooling it is extracted with water, the organic phase is separated and extracted several times with 2N HCl. The combined hydrochloric phases are neutralized with sodium bicarbonate and extracted several times with methylene chloride. Then the combined methylene chloride phases are extracted with 2N HCl. The organic phase is separated, dried and evaporated. The remaining hydrochloride of the title compounds is crystallized with a small amount of acetone, cooled to −20° C., sucked off and recrystallized twice with activated charcoal from acetone.

Yield: 1.63 g (52.6%); m.p. 117°–118° C.

EXAMPLE 2

1-[3-(2-Diethylaminoethoxy)-4-methyl-2-thienyl]-3-phenyl-1-propanone hydrochloride (a) Liberation of 2-diethylaminoethylchloride 800 ml of diethylcarbonate, 160.0 g (929.7 mmoles) of 2-diethylaminoethylchloride hydrochloride, 100 ml of a saturated solution of $Na_2CO_3$ and 120 g of $Na_2CO_3$ are stirred in a 2 l Erlenmeyer flask. The diethylcarbonate phase is decanted into a separatory funnel, separated, dried with $Na_2SO_4$ and filtered into a dropping funnel.

(b) O-Alkylation 28.5 g (115.7 mmoles) of 1-(3-hydroxy-4-methyl-2-thienyl)-3-phenyl-1-propanone are dissolved in 280 ml of diethylcarbonate (DEC). 120 ml (120 mmoles) of 1N NaOMe are added drop by drop and distilled off by means of a small MeOH bridge up to a bottom temperature of 90° C. The reaction mixture is allowed to cool to a temperature of about 50° C. Then the solution of 2-diethylaminoethylchloride in diethylcarbonate is added drop by drop. Then the reaction temperature is maintained at 90° C. for 40 minutes.

(c) Working up of the free end product

The reaction mixture is added with stirring and partitioned between 500 ml of ethylacetate and 50 ml of $NaHCO_3$ solution. The aqueous phase is reextracted with ethylacetate (2×200 ml).

The organic phase is dried with $Na_2SO_4$ and stirred with activated charcoal and filtered. The solution is added with stirring and sucked off. 37.5 g of an amber oil are obtained (100% of theory).

(d) Reaction to yield the hydrochloride

The oil is taken up into 200 ml of $CHCl_3$ and 200 ml of ether. Then dry HCl is passed, until the solution reacts acidicly on wet pH-paper (25 minutes). The solution is added with stirring and sucked off. The resulting oil is crystallized with 50 ml of acetone, maintained in a refrigerator for 3 hours, sucked off and digested with acetone (2×25 ml). The crude product is recrystallized twice from acetone (with activated charcoal).

Yield: 23.77 g (58.72%).

The obtained compound corresponds to the product of Example 1.

The compounds of formula (I) mentioned in the following Table may be prepared according to the above process.

TABLE

| R | $R_1$ | $R_2$ | $R_3$ |
|---|---|---|---|
| H, $CH_3$ | H, $CH_3$ | $CH_3$ | $CH_3$ |
| H, $CH_3$ | H, $CH_3$ | $CH_3$ | $CH_2-CH_3$ |
| H, $CH_3$ | H, $CH_3$ | $CH_3-CH_2$ | $CH_3-CH_2$ |
| H, $CH_3$ | H, $CH_3$ | $CH_3-CH_2$ | $CH_3-CH_2-CH_2-$ |
| H, $CH_3$ | H, $CH_3$ | $CH_3-CH_2-CH_2$ | $CH_3-CH_2-CH_2-$ |
| H, $CH_3$ | H, $CH_3$ | $-CH_2-CH=CH_2$ | $CH_3$ |
| H, $CH_3$ | H, $CH_3$ | $-CH_2-CH=CH_2$ | $CH_2-CH_3$ |
| H, $CH_3$ | H, $CH_3$ | $-CH_2-CH=CH_2$ | $-CH_2-CH=CH_2$ |
| H, $CH_3$ | H, $CH_3$ | $-(CH_2)_4-$ | |
| H, $CH_3$ | H, $CH_3$ | $-(CH_2)_5-$ | |
| H, $CH_3$ | H, $CH_3$ | $-(CH_2)_6-$ | |
| H, $CH_3$ | H, $CH_3$ | $-(CH_2)_2-O-(CH_2)_2-$ | |
| H, $CH_3$ | H, $CH_3$ | $-(CH_2)_2-N(CH_3)-(CH_2)_2-$ | |

EXAMPLE 3

1-[3-(2-Diethylaminoethoxy)-4-methyl-2-thienyl]-3-phenyl-1-propanone (I) ($R_1$=H, $R_2$=$CH_3$, $R_2$ and $R_3$=ethyl)

2.0 g (5.24 mmoles) of 1-[3-(2-diethylaminoethoxy-4-methyl-2-thienyl]-2-phenyl-1-propanone hydrochloride are partitioned between 20 ml of a saturated sodium bicarbonate solution and 20 ml of methylene chloride. The organic phase is separated, dried and evaporated. The oily residue is distilled in the bulb tube at a pressure of 0.01 mbar and at a temperature of 185° C. (air bath temperature).

Yield: 1.45 g (80%) of a colorless oil.

EXAMPLE 4

1-[3-(2-Dimethylaminoethoxy)-4-methyl-2-thienyl]-3-phenyl-1-propanone 34.5 g (0.24 moles) of 1-chloro-2-dimethylaminoethane hydrochloride are stirred with a saturated $Na_2CO_3$-solution of 108 g of $Na_2CO_3$ (1 mole) in 250 ml of water and 150 ml of diethyl carbonate (DEC) for 30 minutes. After decanting the amine solution it is stirred again with 90 ml of diethylcarbonate for 10 minutes. Then the combined amine solutions are dried over anhydrous sodium sulfate and sodium carbonate.

The dried amine solution is added to 8.1 g (0.03 moles) of sodium phenolate (prepared by dissolving phenol in the equivalent amount of methanolic sodium methylate solution and subsequent evaporation up to a constant weight) and heated to 90° C. with stirring and exclusion of water (KOH-drying tube) for 45 minutes. After cooling of the solution the reaction mixture is sucked off through a glass frit so as to remove the precipitated salt, and the solution is evaporated in vacuo.

The oily residue is taken up into 100 ml of methylene chloride and extracted with 0.5N NaOH (4 times with 20 ml each time) and with water (3 times with 10 ml each time) and reextracted with 10 ml of methylene chloride. The combined $CH_2Cl$-phases are shaken intensively with 20 ml of 4N HCl and then with 5 ml of water. The aqueous phase is reextracted with 5 ml of methylene chloride. The combined methylene chloride phases are dried over $Na_2SO_4$ and evaporated.

The oily crude product (13.2 g) is treated in about 500 ml of acetone with activated charcoal. 7.85 g (73.5% based on phenol) of 1-[3-(2-dimethylaminoethoxy)-4-methyl-2-thienyl]-3-phenyl-1-propanone hydrochloride are obtained, m.p. 106°–108° C. (acetone).

DC: Polygram SIL G/$UV_{254}$
Eluent: toluene:ethanol:concentrated ammonia=9:3:0.3
end product visible: UV; Rf about 0.75
amine visible: $I_2$-vapors
phenol visible: UV; 5% $FeCl_3$ in 1N HCl

EXAMPLE 5

1-[3-(2-Piperidinylethoxy)-4-methyl-2-thienyl]-3-phenyl-1-propanone hydrochloride The process of Example 4 is repeated, however, using 15 g (0.082 moles) of 1-(2-chloroethylpiperidine) (m.p. of the hydrochloride 230°–233° C. (dec.) (subl. 140°–190° C.); lit. 230°–233° C.; F. H. Clarke, J. Org. Chem. 26, 1126–32 (1961)), first 100 ml of DEC and then 30 ml of DEC and 36 g (0.34 moles) of $Na_2CO_3$ in 100 ml of water.

The dried amine solution is heated at 90° C. together with 2.7 g (0.010 moles) of sodium phenolate with stirring and exclusion of moisture for 1 hour.

The reaction mixture is worked up in the manner described in Example 4. Thus 3.25 g of 1-[3-(2-piperidinylethoxy)-4-methyl-2-thienyl]-3-phenyl-1-propanone hydrochloride (82%, based on phenol) are obtained, m.p. 93°–95° C. (acetone).

DC: Polygram SIL G/UV 0.67
Eluent: toluene:ethanol:concentrated ammonia=9:3:0.3
Rf about 0.67.

EXAMPLE 6

1-[3-(2-Pyrrolidylethoxy)-4-methyl-2-thienyl]-3-phenyl-1-propanone hydrochloride The process of Example 4 is repeated, however, using 13.6 g (0.08 moles) of 1-(2-chloroethyl)-pyrrolidine hydrochloride (m.p. 173°–174° C., beginning with 125° C. partially sublimation and rearrangement; lit. 173.5°–174° C.; J. Am. Chem. Soc. 70 (1948), 3098–3100, J. B. Wright; Beilstein 20/IV/66), first 100 ml of DEC and then 30 ml of DEC and 37.5 g of $Na_2CO_3$ in 100 ml of water.

The dried amine solution is heated at 90° C. together with 2.7 g (0.010 moles) of sodium phenolate with stirring and exclusion of moisture.

The reaction mixture is worked up as described in Example 4. 2.1 g of 1-[3-pyrrolidylethoxy-4-methyl-2-thienyl]-3-phenyl-1-propanone hydrochloride are obtained (55%, based on phenol), m.p. 84°–86° C. (acetone).

DC: Polygram SIL G/UV 254
Eluent: toluene:ethanol:concentrated ammonia=9:3:0.3
Rf about 0.63.

EXAMPLE 7

1-[3-(2-(4-Morpholinyl)-ethoxy)-4-methyl-2-thienyl]-3-phenyl-1-propanone hydrochloride The process of Example 4 is repeated, however, using 15 g of 4-(2-chloroethyl)-morpholine hydrochloride (m.p. 184°–185° C., subl. beginning with 150° C., lit. 178°–180° C. and 182°–182,5° C. respectively; F. Leonhard, H. Horn; J. Am. Chem. Soc. 78, 1199–1201 (1956); J. P. Mason, H. W. Block; J. Am. Chem. Soc. 62, 1445 (1940)) in 100 ml of diethyl carbonate and 35 g of sodium carbonate in 250 ml of water.

The dried amine solution is heated at 90° C. together with 2.7 g (0.01 mole) of sodium phenolate with stirring and exclusion of moisture. The solution is sucked off through a glass frit to remove the precipitated salt and the solution is evaporated in vacuo. The oily residue is taken up into 150 ml of methylene chloride, extracted with 0.5N NaOH (4 times with 20 ml each time) and reextracted with water (3 times with 15 ml each) and methylene chloride (10 ml). The methylene chloride phase dried over $Na_2SO_4$ yields 3.3 g of an oily crude product. The free base is purified by means of a silicagel column pretreated with petrol ether (40/60)/ether/triethylamine = 10/3/1. After elution with methylene chloride, concentration of the methylene chloride phase, extraction with 4N HCl, drying and evaporation 1.5 g of 1-[3-(2-(4-morpholinyl)-ethoxy)-4-methyl-2-thienyl]-3-phenyl-1-propanone hydrochloride are obtained (37.6% of the theory, based on phenol), m.p. (acetone-diisopropylether) 113°–115° C.

DC/Rf = 0.65

EXAMPLE 8

Pharmacological properties of the compounds of the invention

1-[3-(2-Diethylaminoethoxy)-4-methyl-2-thienyl]-3-phenyl-1-propanone hydrochloride was tested as representative compound as to its antiarrhythmic activity and its effect on the circulatory system. The extension of the effective refactory period was used as criterion in judging the antiarrhythmic activity. The effect on the contractile power was a parameter of the effect on the circulatory system.

Quinidine and lidocaine were used as comparative substances, which are typical antiarrhythmics having Na-antagonizing effect.

TEST METHOD

The studies were made on isolated left atria and papillary muscles of the right ventriculum of quinea pigs having a weight of about 250 to 500 g. In the studies on the papillary muscle a Tyrode solution having a high content of potassium was added to the organ bath solution. The measurement of the functional refractory period (RP) was carried out by means of the double stimulus stimulation (Govier 1975). Rectangular pulses with a duration of 3 msec and a basic frequency of 2 Hz were used. For measuring the effective RP double stimuli were used, i.e. a basic stimulus was followed by an identical second stimulus, the temporal delay of which can be varied exactly. In the measuring procedure the interval between the two pulses is increased as long as also the second stimulus is replied by a contaction of the atrium musculature.

The temporal course of the effect of single doses was monitored and also the dose-effect-curve was established for the substances. In addition to the effect on the effective refractory period also the effect on the contractile power was measured.

1-[3-(2-Diethylaminoethoxy)-4-methyl-2-thienyl]-3-phenyl-1-propanone hydrochloride was added in a concentration of 10 $\mu$M to the organ bath and quinidine and lidocaine were added in a concentration of 100 $\mu$M to the organ bath. Additionally a control without addition of substance was carried out. The test on the partially depolarized papillary muscle was carried out in an organ bath containing also 22 mM of potassium, whereby not only the slow Na-Ca-channels are inactivated, but also the rapid Na-channels. This model seems to be suitable for studying the negative inotropic effect of the antiarrhythmics tested on the atrium.

RESULTS

Quinidine (100 $\mu$M) effected an extension of the RP by 161% within 30 minutes. Lidocaine in the same concentration extended the RP only by 63%. The contractile power of the atrium was lowered by quinidine to 23% within 60 minutes, whereas lidocaine effected a lowering to a maximum of 83%.

1-[3-(2-Diethylaminoethoxy)-4-methyl-2-thienyl]-3-phenyl-1-propanone hydrochloride (10 $\mu$M) extended the RP of the atrium by 128% within 60 minutes, the contractile power was lowered only slightly to 89% and corresponds therewith to the lowering of the contractile power which was observed also under control conditions, i.e. without addition of substance within 60 minutes. It is remarkable that 1-[3-(2-diethylaminoethoxy)-4-methyl-2-thienyl]-3-phenyl-1-propanone hydrochloride demonstrated already in a concentration of 3 $\mu$M an extension of the RP by 73% without lowering the contractile power simultaneously.

On the partially depolarized papillary muscle in which the effect on the blockage of Na-channels of different substances may be studied, it was demonstrated that 1-[3-(2-diethylaminoethoxy)-4-methyl-2-thienyl)]-3-phenyl-1-propanone hydrochloride showed an activity still independent on the Na-antagonism.

SUMMARY

1-[3-(2-diethylaminoethoxy)-4-methyl-2-thienyl]-3-phenyl-1-propanone hydrochloride is characterized by an especially favourable relationship between its antiarrhythmic effect and the negative inotropic effect. In a concentration of 10 $\mu$M it decreases the excitability and causes an extension of the refractory period, the contractile power of the atrium being inhibited slightly. Additionally it could be demonstrated on the partially depolarized papillary muscle that the effect of 1-[3-(2-diethylaminoethoxy)-4-methyl-2-thienyl]-3-phenyl-1-propanone hydrochloride could lie also in an effect independent on the attack at the Na-channel. With such an characteristic of effects 1-[3-(2-diethylaminoethoxy)-4-methyl-2-thienyl]-3-phenyl-1-propanone hydrochloride differs fundamentally from the comparative substances.

The invention now being fully described, it will be apparent to one of ordinary skill in the art that many changes and modifications can be made without departing from the spirit or scope of the invention as set forth herein.

The present disclosure relates to the subject matter disclosed in Austrian patent application No. A 2870/86 filed on Oct. 29th, 1986, the entire specification of which is incorporated herein by reference.

What is claimed is:

1. A 1-[3-(2-Dialkylaminoethoxy)-2-thienyl]-3-phenyl-1-propanone of the formula

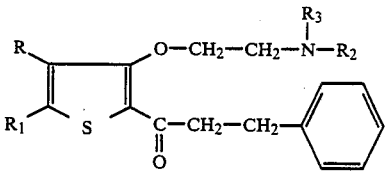

and pharmaceutically acceptable acid addition salts thereof, wherein

R and $R_1$ each are hydrogen or methyl, $R_2$ and $R_3$, which are the same or different, each are alkyl, cycloalkyl, alkenyl or alkynyl each containing up to 8 carbon atoms, or $R_2$ and $R_3$ together with the nitrogen atom to which they are attached form a 5 to 7-membered saturated ring or a saturated heterocyclic ring which may contain optionally an oxygen or nitrogen atom as further hetero atom in the ring, a further nitrogen atom being unsubstituted or substituted by an alkyl radical containing 1 to 3 carbon atoms.

2. The phenyl-1-propanone of claim 1, being 1-[3-(2-diethylaminoethoxy)-4-methyl-2-thienyl]-3-phenyl-1-propanone or the hydrochloride thereof.

3. The phenyl-1-propanone of claim 1, being 1-[3-(2-dimethylaminoethoxy)-4-methyl-2-thienyl]-3-phenyl-1-propanone hydrochloride.

4. The phenyl-1-propanone of claim 1, being 1-[3-(2-piperidinylethoxy)-4-methyl-2-thienyl]-3-phenyl-1-propanone hydrochloride.

5. The phenyl-1-propanone of claim 1, being 1-[3-(2-pyrrolidylethoxy)-4-methyl-2-thienyl]-3-phenyl-1-propanone hydrochloride.

6. The phenyl-1-propanone of claim 1, being 1-[3-(2-(4-morpholinyl)-ethoxy-4-methyl-2-thienyl]-3-phenyl-1-propanone hydrochloride.

7. The phenyl-1-propanone of claim 1, being an acid addition salt from an acid selected from the group consisting of
hydrochloric acid,
hydrobromic acid,
phosphoric acid,
sulfonic acid,
citric acid,
acetic acid,
succinic acid,
maleic acid,
p-toluene sulfonic acid, and
methanesulfonic acid.

8. A pharmaceutical composition, comprising an antiarrhythmic amount of the phenyl-1-propanone of claim 1 and a pharmaceutically acceptable carrier.

9. The pharmaceutical composition of claim 8, wherein the phenyl-1-propanone is present in an amount between about 100 mg and 200 mg.

10. The pharmaceutical composition of claim 8, in dosage unit form.

11. The composition of claim 8 in oral form.

12. The composition of claim 8, in a form selected from the group consisting of
tablets,
slow-release mixtures, and
capsules.

13. A method of treating a cardiac arrhythmia, comprising administering to a patient in need of such treatment the composition of claim 8.

14. The method of treating a cardiac arrhythmia of claim 13, wherein the arrhythmia is selected from the group consisting of
supraventricular tachycardia,
ventricular tachycardia,
ventricular ectopia, and
reentry tachycardia.

* * * * *